US012667420B2

(12) United States Patent
Qian et al.

(10) Patent No.: US 12,667,420 B2
(45) Date of Patent: Jun. 30, 2026

(54) CATHETER ABLATION DEVICE WITH IMPEDANCE MONITORING

(71) Applicants: The University of Sydney, New South Wales (AU); Western Sydney Local Health District, New South Wales (AU)

(72) Inventors: Pierre Qian, New South Wales (AU); Michael Anthony Barry, New South Wales (AU)

(73) Assignees: The University of Sydney, New South Wales (AU); Western Sydney Local Health District, New South Wales (AU)

( * ) Notice: Subject to any disclaimer, the term of this patent is extended or adjusted under 35 U.S.C. 154(b) by 1022 days.

(21) Appl. No.: 17/171,837

(22) Filed: Feb. 9, 2021

(65) Prior Publication Data

US 2021/0186609 A1 Jun. 24, 2021

Related U.S. Application Data

(63) Continuation of application No. PCT/AU2019/050844, filed on Aug. 13, 2019.

(30) Foreign Application Priority Data

Aug. 13, 2018 (AU) ................................ 2018902954

(51) Int. Cl.
 *A61B 18/18* (2006.01)
 *A61B 18/00* (2006.01)
(52) U.S. Cl.
 CPC ..................... *A61B 18/1815* (2013.01); *A61B 2018/00577* (2013.01); *A61B 2018/00875* (2013.01);

(Continued)

(58) Field of Classification Search
 None
 See application file for complete search history.

(56) References Cited

U.S. PATENT DOCUMENTS 4,920,980 A 5/1990 Jackowski
5,328,471 A 7/1994 Slepian
 (Continued)

FOREIGN PATENT DOCUMENTS

AU 2006292698 A1 3/2007
CN 101969875 A 2/2011
 (Continued)

OTHER PUBLICATIONS

U.S. Appl. No. 16/994,134, "Non-Final Office Action", Oct. 24, 2023, 7 pages.
 (Continued)

*Primary Examiner* — Sean W Collins
*Assistant Examiner* — Nora W Rhodes
(74) *Attorney, Agent, or Firm* — Kilpatrick Townsend & Stockton LLP

(57) ABSTRACT

The invention relates to a catheter ablation device for delivery of energy (such as microwave energy) via a radiating antenna to a selected region of tissue, the device having an elongated catheter with an outer sheath, configured to allow flow of fluid along the catheter to exit through one or more orifices adjacent to the antenna. The device includes an impedance monitoring system having two electrodes arranged respectively inside and outside said catheter sheath, the impedance monitoring system including an electric circuit incorporating an ionic conductivity path through said fluid. The device is introduced into a blood vessel and the invention allows monitoring of changes in the size of the blood vessel during an ablation procedure, as it can be used to measure the impedance of an electrical circuit including (Continued)

a blood path in the blood vessel in the region of the ablation, the measured impedance providing a measure of vascular calibre.

12 Claims, 7 Drawing Sheets

(52) U.S. Cl.
CPC .................. *A61B 2018/1823* (2013.01); *A61B 2018/1861* (2013.01); *A61B 2218/002* (2013.01)

(56) References Cited

U.S. PATENT DOCUMENTS

| | | | |
|---|---|---|---|
| 5,662,680 A | 9/1997 | Desai | |
| 6,027,500 A | 2/2000 | Buckles et al. | |
| 6,210,367 B1 | 4/2001 | Carr | |
| 6,635,055 B1 | 10/2003 | Cronin | |
| 7,566,341 B2 | 7/2009 | Keller et al. | |
| 8,382,750 B2 | 2/2013 | Brannan | |
| 11,324,408 B2 | 5/2022 | Wang | |
| 11,701,158 B2* | 7/2023 | Chou ........................ | A61B 8/12 |
| | | | 606/1 |
| 2004/0049254 A1 | 3/2004 | Longo | |
| 2005/0267463 A1 | 12/2005 | Vanney | |
| 2007/0066972 A1 | 3/2007 | Ormsby et al. | |
| 2007/0203551 A1 | 8/2007 | Cronin et al. | |
| 2008/0183169 A1 | 7/2008 | Klimovitch et al. | |
| 2008/0294041 A1 | 11/2008 | Kassab | |
| 2009/0062684 A1 | 3/2009 | Gregersen et al. | |
| 2009/0240249 A1 | 9/2009 | Chan et al. | |
| 2010/0069921 A1 | 3/2010 | Miller et al. | |
| 2010/0198040 A1 | 8/2010 | Friedman et al. | |
| 2010/0262137 A1 | 10/2010 | Nye et al. | |
| 2011/0040162 A1 | 2/2011 | Kinnison | |
| 2011/0082383 A1 | 4/2011 | Cory et al. | |
| 2011/0291736 A1 | 12/2011 | Klimovitch et al. | |
| 2011/0306867 A1 | 12/2011 | Gopinathan et al. | |
| 2012/0116486 A1 | 5/2012 | Naga et al. | |
| 2012/0157988 A1 | 6/2012 | Stone et al. | |
| 2012/0259326 A1 | 10/2012 | Brannan et al. | |
| 2012/0265200 A1 | 10/2012 | Curley | |
| 2013/0226169 A1 | 8/2013 | Miller et al. | |
| 2013/0296840 A1 | 11/2013 | Condie et al. | |
| 2014/0018788 A1 | 1/2014 | Engelman et al. | |
| 2014/0046174 A1 | 2/2014 | Ladtkow et al. | |
| 2014/0257130 A1 | 9/2014 | Cao et al. | |
| 2014/0276743 A1* | 9/2014 | Curley ............... | A61B 18/1815 |
| | | | 606/33 |
| 2015/0080875 A1 | 3/2015 | Kasprzyk et al. | |
| 2015/0105765 A1 | 4/2015 | Panescu et al. | |
| 2016/0081744 A1 | 3/2016 | Wang | |
| 2016/0095535 A1 | 4/2016 | Hettrick et al. | |
| 2016/0184008 A1 | 6/2016 | Papaioannou et al. | |
| 2016/0199127 A1 | 7/2016 | Prutchi | |
| 2016/0242667 A1 | 8/2016 | Fay et al. | |
| 2016/0262777 A1 | 9/2016 | Stigall et al. | |
| 2017/0095290 A1 | 4/2017 | Sherman et al. | |
| 2017/0143414 A1 | 5/2017 | Sliwa et al. | |
| 2017/0252101 A1 | 9/2017 | Hata et al. | |
| 2017/0354364 A1 | 12/2017 | Bar-Tal et al. | |
| 2018/0125575 A1 | 5/2018 | Schwartz et al. | |
| 2018/0289284 A1 | 10/2018 | Panescu et al. | |
| 2018/0338703 A1 | 11/2018 | Sulkin et al. | |
| 2019/0167147 A1* | 6/2019 | Kassab ................ | A61B 5/0215 |
| 2019/0374285 A1 | 12/2019 | Hancock et al. | |
| 2020/0375658 A1 | 12/2020 | Qian et al. | |
| 2021/0186608 A1 | 6/2021 | Qian et al. | |
| 2021/0196378 A1 | 7/2021 | Qian et al. | |
| 2021/0251688 A1 | 8/2021 | Dickhans et al. | |
| 2021/0401495 A1 | 12/2021 | Qian et al. | |

FOREIGN PATENT DOCUMENTS

| | | | |
|---|---|---|---|
| CN | 103096826 A | 5/2013 | |
| CN | 103860266 A | 6/2014 | |
| CN | 105263432 A | 1/2016 | |
| CN | 103096826 B | 7/2016 | |
| EP | 2460486 A1 | 6/2012 | |
| GB | 250673 A | 4/1926 | |
| JP | 57187505 U | 11/1982 | |
| JP | 6216755 A | 1/1987 | |
| JP | 08187297 A | 7/1996 | |
| JP | 2002065693 A | 3/2002 | |
| JP | 2003514635 A | 4/2003 | |
| JP | 2009285463 A | 12/2009 | |
| JP | 2011511424 A | 4/2011 | |
| JP | 2011511538 A | 4/2011 | |
| JP | 2012506300 A | 3/2012 | |
| JP | 2014525814 A | 10/2014 | |
| JP | 2016532497 A | 10/2016 | |
| JP | 2018522612 A | 8/2018 | |
| JP | 2019500170 A | 1/2019 | |
| JP | 2021531841 A | 11/2021 | |
| WO | 9835611 A1 | 8/1998 | |
| WO | 9849957 A1 | 11/1998 | |
| WO | 9956642 A1 | 11/1999 | |
| WO | 0035363 A1 | 6/2000 | |
| WO | 02061880 A2 | 8/2002 | |
| WO | 2009094392 A2 | 7/2009 | |
| WO | 2009098513 A1 | 8/2009 | |
| WO | 2011060200 A1 | 5/2011 | |
| WO | 2012058434 A1 | 5/2012 | |
| WO | 2014188430 A2 | 11/2014 | |
| WO | 2016054379 A1 | 4/2016 | |
| WO | 2016090175 A1 | 6/2016 | |
| WO | 2016197206 A1 | 12/2016 | |
| WO | 2017056056 A1 | 4/2017 | |
| WO | 2017093926 A1 | 6/2017 | |
| WO | 2018023132 A1 | 2/2018 | |
| WO | 2018027174 A1 | 2/2018 | |
| WO | 2018081540 A1 | 5/2018 | |

OTHER PUBLICATIONS

U.S. Appl. No. 17/142,943, "Non-Final Office Action", Oct. 18, 2023, 14 pages.
U.S. Appl. No. 17/171,878, "Non-Final Office Action", Nov. 21, 2023, 13 pages.
CN202080027495.0, "Office Action", Dec. 26, 2023, 12 pages.
JP2021-549554, "Office Action", Dec. 1, 2023, 11 pages.
Chen, et al., "Renal Artery Vasodilation May Be An Indicator of Successful Sympathetic Nerve Damage During Renal Denervation Procedure", Scientific Reports, vol. 6, No. 37218, Nov. 16, 2016, pp. 1-10.
JP2020-572968, "Japanese Office Action", May 11, 2023, pp. 1-7.
Chen, et al., "Renal Artery Vasodilation May Be An Indicator of Successful Sympathetic Nerve Damage During Renal Denervation Procedure", Scientific Reports, vol. 6, Nov. 16, 2016, pp. 1-10.
Doltra, et al., "Effects of Renal Denervation on Renal Artery Function in Humans: Preliminary Study", Plos One, vol. 11, No. 3, Mar. 22, 2016, pp. 1-14.
PCT/AU2019/050844, "International Search Report and Written Opinion", Oct. 24, 2019, 9 pages.
JP2020572955, "Office Action", May 22, 2023, pp. 1-11.
201980053897.5, "CN Office Action", Nov. 20, 2023, pp. 1-15.
19850301.3, "European Search Report", Apr. 8, 2022, pp. 1-7.
U.S. Appl. No. 17/142,943, "Advisory Action", Aug. 22, 2024, 3 pages.
U.S. Appl. No. 17/142,943 , Non-Final Office Action, Mailed On Oct. 24, 2024, 16 pages.
U.S. Appl. No. 17/468,420 , Non-Final Office Action, Mailed On Nov. 7, 2024, 12 pages.
U.S. Appl. No. 17/142,943, "Final Office Action", Jun. 5, 2024, 18 pages.
U.S. Appl. No. 17/468,420, "Non-Final Office Action", Jun. 6, 2024, 14 pages.

(56)          References Cited

OTHER PUBLICATIONS

U.S. Appl. No. 17/142,943, "Final Office Action", Apr. 10, 2025, 24 pages.
U.S. Appl. No. 17/468,420, "Final Office Action", Apr. 18, 2025, 14 pages.
U.S. Appl. No. 17/468,420, "Non-Final Office Action", Apr. 6, 2026, 40 pages.

\* cited by examiner

CATHETER ABLATION DEVICE WITH IMPEDANCE MONITORING

CROSS-REFERENCES TO RELATED APPLICATIONS

This application claims priority to and is a continuation of International Patent Application No. PCT/AU2019/050844, filed Aug. 13, 2019; which claims priority from AU Patent Application No. 2018902954, filed Aug. 13, 2018. The entire contents of each of the PCT/AU2019/050844 and the 2018902954 applications are hereby incorporated by reference in their entirety for all purposes.

FIELD OF THE INVENTION

This invention relates to a catheter ablation device and a method of using such device. The device may be a microwave ablation device, with application in the field of endovascular sympathectomy or denervation such as renal artery denervation. The invention may also find application in other fields of medical ablation including the treatment of atrial and ventricular arrhythmias.

BACKGROUND OF THE INVENTION

Hypertension is a significant medical condition that leads to morbidity and mortality from end organ injury, such as strokes, heart attack and kidney failure. Many patients require multiple medications for blood pressure control and, for some patients, medications are poorly tolerated or ineffective altogether. Renal artery denervation by radiofrequency catheter ablation has emerged as a possible treatment option to control hypertension in these patients who are refractory or intolerant of medical therapy. The procedure aims to eliminate the efferent and afferent nerves that relay neural messages between the kidneys and the central nervous system, as these form essential components of neurohormonal reflexes that elevate blood pressure. The efferent and afferent nerves travel in the outer layer (i.e. adventitia) of the renal artery and the perinephric fat, mostly between 1 and 6 mm from the inner (luminal) surface of the renal arteries, and these nerves can potentially be destroyed by endovascular catheter ablation.

More recently, microwave ablation techniques have been proposed for vascular denervation, and the inventors of the present inventions have demonstrated very effective outcomes in trials of a microwave ablation device as described in WO2016/197206, the entire contents of which are included herein by reference.

Development of this concept has confirmed that microwave ablation using endovascular catheters has applications for renal denervation in the treatment of hypertension as well as cardiac ablation in the treatment of arrhythmias. Microwave heating is radiant and can penetrate deeply into tissue, creating large thermal lesions of more uniform temperature distribution than radiofrequency ablation. The technique does not require any catheter tip-to-tissue contact to produce heating.

Any discussion of documents, acts, materials, devices, articles and the like in this specification is included solely for the purpose of providing a context for the present invention. It is not suggested or represented that any of these matters formed part of the prior art base or were common general knowledge in the field relevant to the present invention as it existed in Australia or elsewhere before the priority date of each claim of this application.

BRIEF SUMMARY OF THE INVENTION

In one form, the present invention provides a catheter ablation device for delivery of energy to a selected region of tissue, the device having an antenna portion including a radiating antenna electrically connectable via an electrical feedline to a source of energy, the antenna configured to generate an electromagnetic field able to ablate tissue in said selected region of tissue, wherein the device comprises an elongated catheter having an outer sheath, the device configured to allow flow of fluid along the catheter to exit through one or more orifices in or adjacent to said antenna portion, wherein the device includes an impedance monitoring system comprising two electrodes, arranged respectively inside and outside said catheter sheath and configured such that in use the impedance monitoring system includes an electric circuit incorporating an ionic conductivity path through said fluid.

When the device is positioned within a blood vessel (or other part of the body), it can be used to measure the impedance of an electrical circuit which includes the blood pool surrounding the catheter sheath, and thus provides a system to monitor changes in calibre of the blood vessel (or other part of the body) during an ablation procedure.

Preferably, the device is a microwave ablation device for delivery of microwave energy, the source of energy comprising a microwave generator. Preferably, the electrodes are arranged proximal of said antenna portion. This ensures the electrodes are substantially outside the microwave field produced by the antenna.

Preferably, the electrodes are electrically connectable to an impedance monitoring means, configured to provide an indication to a user of the device of a measure of the impedance of said electric circuit.

One or both of the internal and external electrodes (being the electrodes arranged inside and outside said catheter sheath, respectively) may comprise ring or part-ring form electrodes. This assists in electrical connection with fluid with which they are in contact.

Said internal electrode may be supported on an outside surface of said electrical feedline.

Said external electrode may be supported on an outside surface of said catheter sheath.

Alternatively, said external electrode may be provided at a location separate from said catheter sheath. For example, it may be supported on a guiding sheath to be used in introducing the device to a patient, or may be provided as a patient return electrode independent of the catheter sheath (introduced to the body independently of the catheter sheath).

In a further form, the present invention provides a method of monitoring changes in vascular calibre during a vascular ablation procedure, comprising introducing a catheter ablation device to a blood vessel at a selected position with respect to a target region of tissue, the catheter ablation device including an impedance monitoring system configured to measure the impedance of an electrical circuit including a blood path in said vessel in or near said selected position, the measured impedance providing a measure of vascular calibre.

Preferably, the catheter ablation device comprises an elongated catheter with an outer sheath having one or more fluid flow openings, the method including:

providing a first electrode inside said catheter sheath and a second electrode outside said catheter sheath;

providing a flow of fluid within said catheter sheath, said fluid flow in electrical contact with said first electrode and passing through said one or more fluid flow openings; and applying a voltage across said electrodes to enable measurement of the impedance there between, said fluid and said blood path both providing part of said electrical circuit.

Embodiments of the invention therefore improve the efficacy and safety of ablation procedures.

BRIEF DESCRIPTION OF THE DRAWINGS

Illustrative embodiments of the various aspects of the present invention will now be described by way of non-limiting example only, with reference to the accompanying drawings. In the drawings.

DETAILED DESCRIPTION OF THE INVENTION

Figure 1:
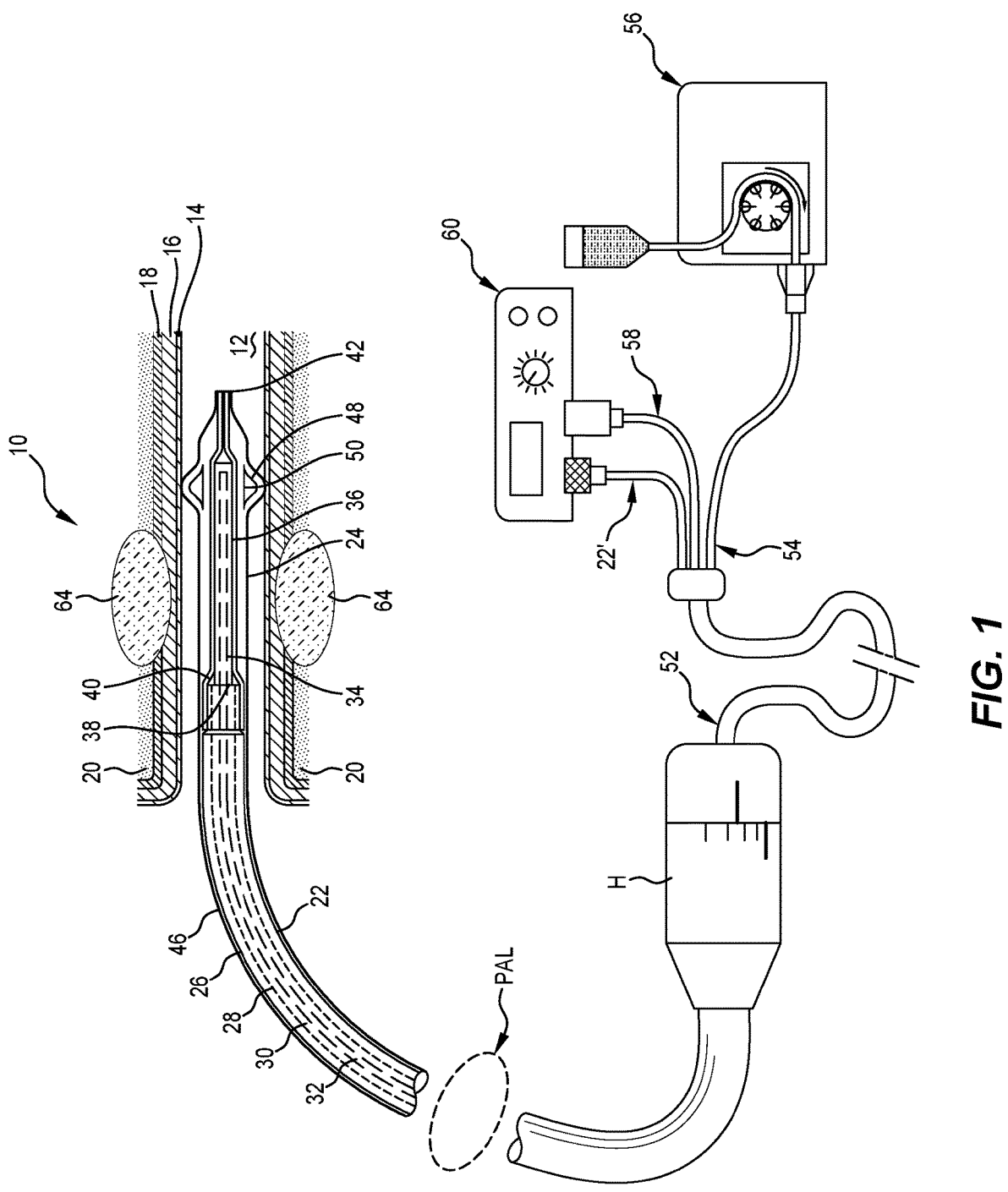
FIG. 1 shows a partial cross-sectional view of a microwave ablation device.

In FIG. 1, microwave ablation device 10 for use in the denervation of renal arteries is shown, comprising an elongate flexible catheter suitable for passage through the vasculature. In particular, device 10 is shown in a renal artery 12, with ablation areas indicated by reference 64.

The various components of device 10 and of artery 12 and surrounding nerves are set out in further detail in WO2016/197206. Other features, including optional components, materials, dimensions, functions, procedural steps and operational parameters are also discussed in that publication.

Of particular note in the context of the present invention are the following components:

Feedline 22, formed by a coaxial cable comprising insulating outer sheath 26, outer conductive shield 28 (e.g. braided copper wire), insulating inner sheath 30 and conductive core 32.

Microwave radiator 24, with radiating element (antenna) 34, formed as a terminal part of the coaxial cable of feedline 22, stripped of its shield and outer insulation sheath. Antenna 34 is positioned within a distal part of device 10 and encased in a tubular sheath 36 to insulate it from its environment.

Feedline 22 and radiator 24 are contained within an outer catheter sheath 46, sized to provide sufficient internal free space around feedline 22, to allow flow of pumped saline solution from a proximal end of the device to the distal end, to act as an irrigant and coolant. The distal ends of antenna sheath 36 and catheter sheath 46 are adhered together at a tip 42.

To provide both a securing and centering function for the device as well as a path for irrigation fluid to exit the device, catheter sheath 46 includes one or more locating formations 48 formed by longitudinal slits 50 arranged in a ring around the sheath (e.g. six slits). The central core of the device (including feedline 22 and antenna 34) are relatively stiff, while sheath 46 is fabricated from a more flexible material. Pulling, at a proximal position, of feedline 22 relative to sheath 46 causes the strips of material of sheath 46 between slits 50 to deform outwardly into convex protrusions to sit against the inner walls 14 of artery 12. Formations 48 are provided at one or more positions along the distal portion of the device, selected to ensure radiator 24 is held in the required location in accordance with the particular application. In FIG. 1 a single distal formation 48 is shown, close to catheter tip 42.

FIG. 1 also shows a structural support cover portion 40, which terminates and seals outer conductive shield 28 and provides an outer layer to sealingly cover the transition between feedline outer sheath 26 and antenna sheath 36, as well as providing structural support for radiator 24 in this portion.

Device 10 may include additional components and functionality, as understood by the skilled person, including those discussed in WO2016/197206.

FIG. 1 also illustrates diagrammatically the proximal end of device 10, connecting outside a percutaneous access location PAL with a handle H, which provides connection with a patient cable 52. Handle H is designed to allow the operator to actuate and control locating formations 48, by relative rotation between two axially separated handle parts causing traction of feedline 22 relative to sheath 46. As FIG. 1 shows, the left hand part of handle H is provided with graduation markings to indicate to the operator the degree of rotation with respect to the indicium on the right hand part, the graduation markings indicating the extent of opening of locating formations 48 (e.g. 5 mm distension). Handle H also provides an interconnection between the relatively thin coaxial feedline 22 which runs to the catheter distal portion and a thicker electrical feedline 22' which runs to the microwave generator, as well as a fluid interconnection between the internal lumen(s) of catheter sheath 46 and a fluid line 54.

At the proximal end of patient cable 52, fluid line 54 connects to a fluid control system 56, which provides the saline irrigation flow though sheath 46, while patient cable feedline 22' connects to an electrical power/control unit 60. Fluid control system 56 includes suitable pump, control and flow measurement means, allowing selective adjustment of fluid flow parameters, and may also be used to introduce other fluids such as drugs and markers into the fluid flow for delivery to the distal end of the catheter device. Electrical unit 60 includes a tunable microwave generating source for delivering power to antenna 34. Electrical cabling 58 provides connection of other electrical components of device 10 (as discussed below) to power, monitoring and control circuitry comprised in electrical unit 60. As will be appreciated, patient cable 52 jackets together all the cores from handle H, for convenient implementation of the device.

Temperature Measurement

Device 10 also includes a means for measuring the temperature of the distal portion of the catheter.

It is known to include in medical catheter devices one or more temperature sensors, such as thermocouples or thermistors. For example, for temperature monitoring using a thermocouple, a catheter is provided with a thermocouple wire pair of two different metals extending from the proximal end, through the catheter shaft and into the distal portion, where the thermocouple hot junction of the wire pair (the temperature measuring point) is located. The ends of each wire are typically stripped of their covering insulation, twisted, soldered and potted into a distal tip electrode. However, particular issues arise with regard to use of this type of device in microwave ablation devices As will be understood from WO2016/197206, microwave heating is radiant and can penetrate deeply into tissue without antenna-tissue contact. The design of the catheter means the radiating antenna is both electrically insulated from the surrounding environment and separated therefrom by a zone of flowing irrigation fluid (saline). This prevents temperature rises at the catheter tip due to ohmic heating and reduces any dielectric heating along the catheter shank, thus enabling higher microwave power to be used without undesirably or uncontrollably high temperatures within the catheter. In this regard, the temperature of the catheter tip should be restricted to a maximum of around 50° C., as above this temperature there are risks of coagulum formation, tissue charring and steam pops, which can cause adverse clinical outcomes. Monitoring temperature in the distal portion of the catheter can therefore be important. Additionally, during microwave renal artery denervation, a temperature sensor in the vicinity of the catheter tip can provide a measure of renal artery blood flow velocity using a thermodilution method. This enables monitoring of arterial patency, required for safe delivery of microwave energy, as well as reduction in renal microvascular resistance, expected to occur with successful renal denervation if the patient has a high renal sympathetic tone (due to innate physiology or otherwise).

A natural consequence of the electrical isolation and fluid surrounding the microwave antenna is the inability to approximate the local tissue temperature by measuring the temperature of the antenna tip.

Figure 2:
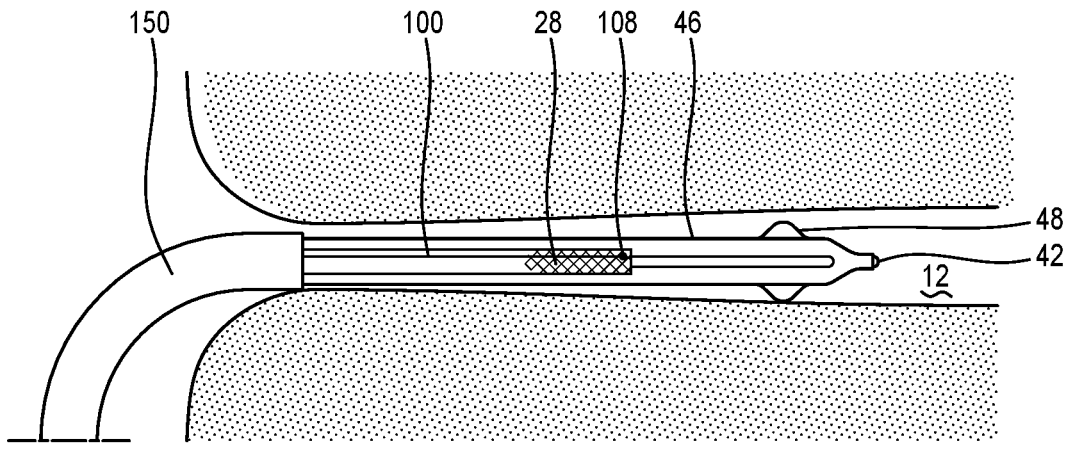
FIGS. 2 and 3 show, in alternative embodiments, a microwave ablation device including a thermocouple arrangement.
Figure 3:
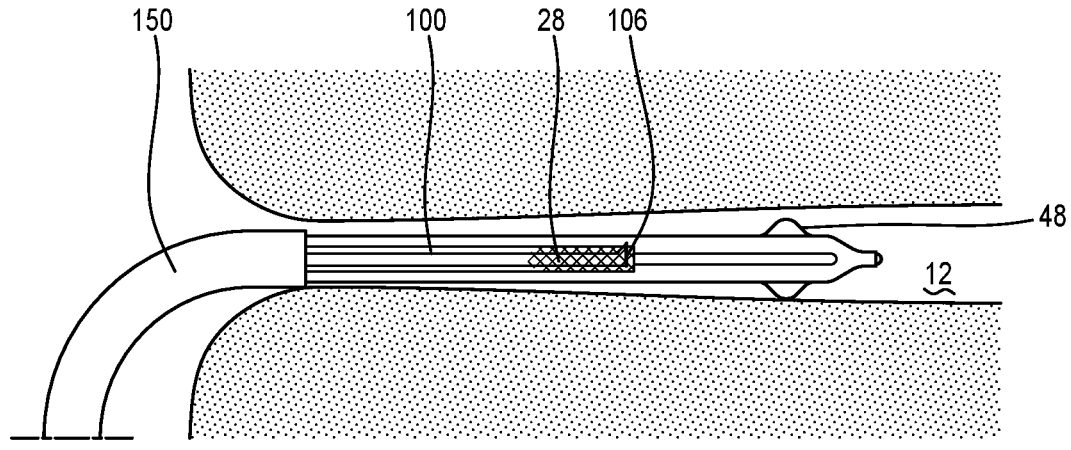

As illustrated in FIGS. 2 and 3, device 10 uses a thermocouple measurement of the temperature at the terminal part of the outer conducting shield 28 of feedline 22. This is provided by electrically connecting a wire at that point 108 to create a thermocouple hot junction. The wire is made from a material with a Seebeck coefficient different to that of shield 28, such that a temperature change at this junction point provides an electrical current that can be used to determine the temperature. In particular, a type-T, copper-constantan material is used, the braided wire of feedline shield 28 being plated copper. This is found to provide a measurement of temperature within an accuracy of approximately 0.5° C. in the temperature range encountered during ablation procedures. As will be understood, the region of highest temperature with the catheter will be distal of this point 108, closer to the longitudinal center of antenna 34, however the distal end 38 of feedline shield braid 28 is sufficiently close to provide an accurate relative measure of this maximum temperature, as discussed further below.

Importantly, this arrangement obviates the need for a second wire (and associated elements such as adhesive) in order to provide the thermocouple. The temperature measurement is taken of the outer shield material itself, close to or at the point where the braid ends, from which the central feedline core extends.

In particular, the hot junction is made by stripping the insulation from the end of the constantan wire, and soldering it to a short end portion 106 (see further detail in FIG. 4B) of the shield braid 28 from which the outer sheath 26 has been removed. In the variant shown in FIG. 3, the end of wire 100 is wrapped around the terminal portion of shield braid 28 before soldering, to create a strong, firm joint, both electrically and structurally.

Wire 100 runs along the length of the catheter and connects via a suitable connector in handle H to patient cable 52 and from there through electrical cabling 58 to electrical power/control unit 60, which includes appropriate circuitry and processing means to calculate the temperature from the measured voltages. In the figures, reference 150 indicates the guiding sheath through which catheter device 10 is introduced.

This thermocouple system provides a means of monitoring heating adjacent to the catheter antenna, in particular to enable the user to avoid excessive temperatures during ablation, such as may result from excessively high power or failure of catheter irrigation flow. Further, monitoring temperature provides a measure of the microwave radiation at the antenna. With higher electrical power reaching the antenna, or as frequency matching between the antenna and its surrounding medium improves, the local temperature increases. Thus the temperature provides an independent measure of microwave emission, additional to measuring reflected power at the microwave generating source.

By way of example, in testing the device of the invention an ablation procedure under deliberately suboptimal conditions was conducted by applying 80 W of microwave power with 10 W of reflected power measured at the generator, this being a result of choosing a poorly matched frequency. With the thermocouple system a temperature at point 108 of 38° C. was measured. Repeating the test with the same forward power and selection of an optimal frequency (reducing the reflected power measured at the generator to zero), a temperature of 44° C. was measured.

As noted above, the temperature at the feedline braid point 108 during ablation correlates with microwave emission from the antenna. Testing of the device also demonstrated an inverse relationship between the reflected power detected by the microwave generator and the measured temperature, providing an additional independent measure of microwave energy emission.

Use of Thermocouple Wire as Pull Wire

Figures 4A, 4B:
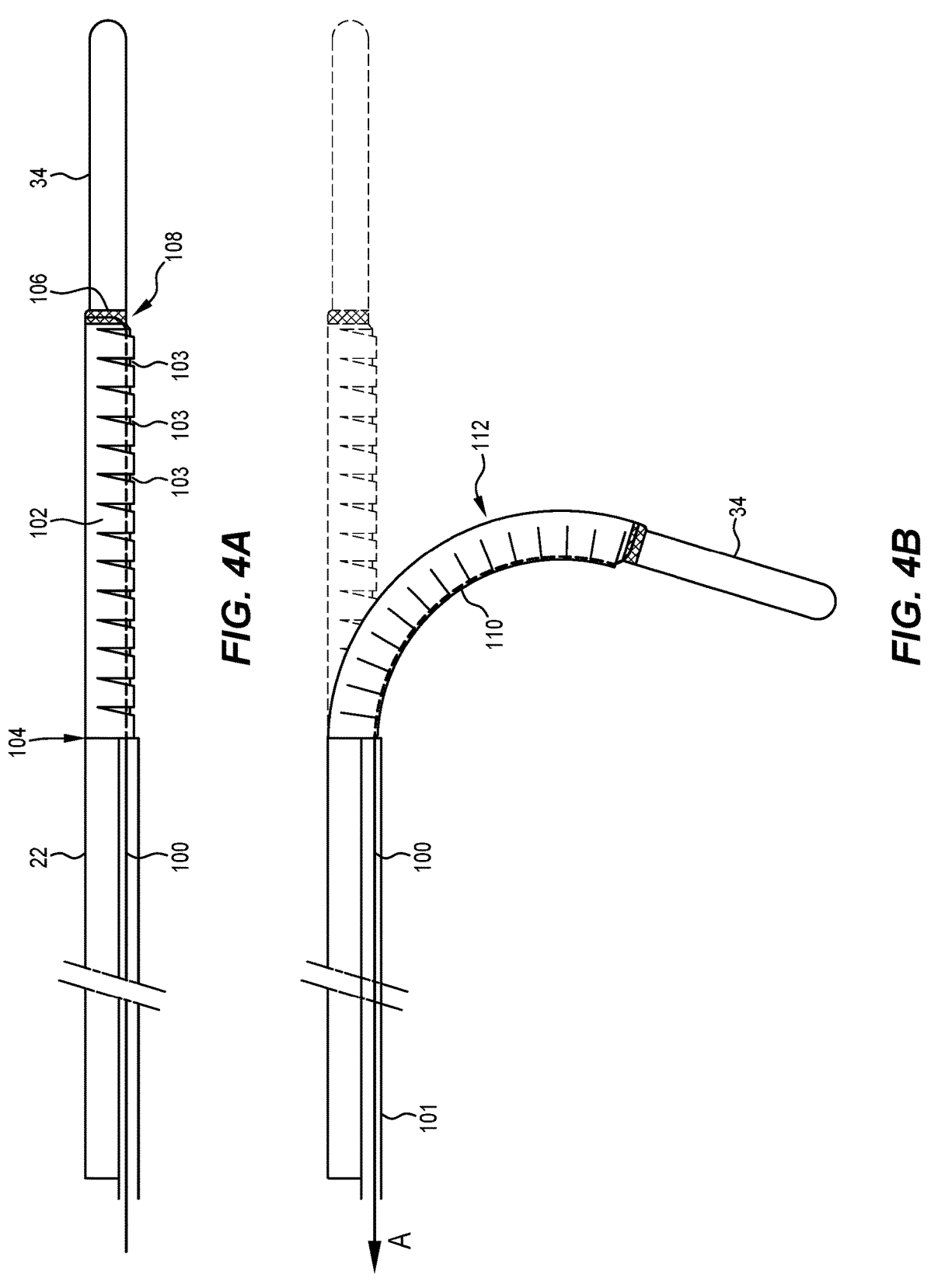
FIGS. 4A and 4B illustrate in further detail a part of the device of FIG. 3, in two configurations.

In accordance with a further embodiment of the invention, the thermocouple wire can be used to serve the double function of temperature monitoring and catheter steering. The detail shown in FIGS. 4A and 4B illustrates use of thermocouple wire 100 as a pull wire, used for flexing and thus steering the distal end of the device during insertion.

To this end, a part of the microwave feedline 22 is provided with a flexion sheath 102, made from a relatively non-compressible material. Flexion sheath 102 encases the feedline from a point 108 at the proximal end of antenna 34 (at the termination of conductive shield 28) to a point 104 where it is anchored to outer sheath 26 of the feedline, a distance of for example 30 mm, defining the longitudinal extent of the desired flexion portion of the catheter. The inner diameter of flexion sheath 102 is larger than the outer diameter of feedline sheath 26, to provide room to accommodate thermocouple wire 100 for longitudinal movement, as discussed below.

Flexion sheath 102 includes along its length on one side a series of regularly spaced flexible striations 103, which may be transverse cuts in the material, or may comprise a soft, flexible material intercalated along the length of the flexion section. In either form, these striations allow flexion sheath 102, on that side only, to readily compress (remaining resistant to compression on the opposite side). This arrangement therefore provides a mechanism comprising a relatively incompressible 'spine' and a compressible arrangement of 'ribs', flexion enabled in the direction opposite the spine.

From point 104, on the same side of the feedline 22, a hollow cable 101 of a relatively non-compressible material (to prevent compression in the axial direction, but generally able to deflect relatively easily in the lateral direction) runs to the proximal part of the catheter, secured to the outer feedline sheath 26 by jacketing within the feedline, or alternatively secured within a lumen of the outer sheath 46. The internal bore of cable 101 is sized to accommodate thermocouple wire 100, and this arrangement ensures the wire is retained close to the feedline core of the catheter.

As FIG. 4A shows, the constantan wire 100 is run along the bore of cable 101 and along the inside of flexion sheath 102, and its terminal portion is then wrapped around the distal end 106 of the conducting braid of feedline shield 28 (one or more times) and electrically joined (by secure soldering) thereto at point 108, to produce the thermocouple hot junction. At this point the distal end of flexion sheath 102 is sealed over this electrical joint so that both of its ends are secured around feedline 22 (at points 104 and 108). Wire 100 is thus free to run freely from this joint point 108 to the proximal part of the catheter where it is arranged for access and manipulation by an operator. A constantan wire is selected having sufficient tensile strength to handle relatively significant tension, allowing it to reliably transfer force to the catheter tip.

Wire 100 thus provides a pull wire function, as known in the general field of deflecting tip catheters. When wire 100 is pulled in direction A, the wire length 110 along this flexion portion shortens, producing flexion of sheath 102 by closing or compressing of the striations 103 and resulting in the bending shown in FIG. 4B. In the configuration 112 of maximum flexion, the striations 103 are fully closed or compressed. As will be understood, the flexion radius can be selected by choosing the particular arrangement and dimensions of the striations 103 of flexion sheath 102, so providing a 'tight curve' or a 'wide curve' catheter, depending on the particular application.

When wire 100 is released, the natural elasticity of the materials of the catheter results in a return to the original, straight configuration. As will be appreciated, the wire is always retained parallel to the axial direction of the catheter along its length, so minimizing the risk of the wire fatiguing at any point.

In this way, the tip of the catheter can be steered by manipulation of thermocouple wire 100, so guiding the catheter into the desired ablation position, without the need to incorporate a separate pull wire in the catheter assembly.

Alternative means of providing the desired directional flexibility of the catheter are of course possible, such as use of a coil-reinforced outer sheath, and/or use of a strip of stainless steel (or similar relatively incompressible material) to provide the spine of the flexion portion, the remainder of this portion of the catheter being of an elastomeric material able to compress as required, the catheter thus able to flex in a direction opposite to the location of the spine.

Temperature Measurement—Trials and Results

Figure 5:
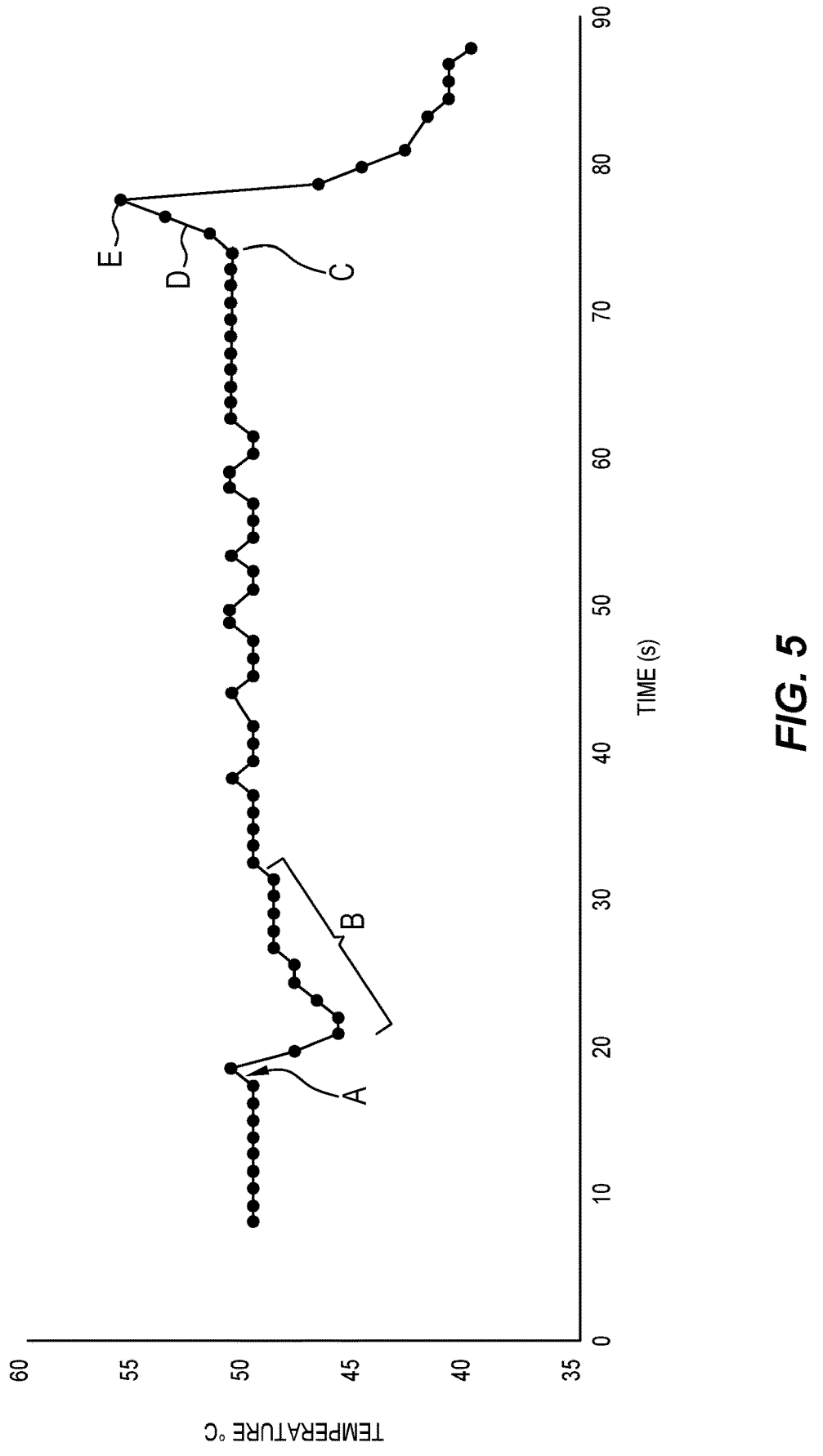
FIGS. 5 and 6 show time-temperature graphs of trials of the device of the invention.

FIG. 5 graphically illustrates measured temperature fluctuations in use of the device of the invention during a 110 W trial ablation procedure, including arterial injection and irrigation failure. These results demonstrate that the device provides a reliable feedback measure of the conditions in the distal portion of the catheter.

The referenced points and phases of the procedure are:
A Renal angiogram
B Thermodilution curve produce by injection of room temperature contrast agent
C Catheter irrigation interrupted
D Resulting sharp rise in temperature
E Microwave ablations stopped As noted above, and as FIG. 5 illustrates (phase B), the temperature monitoring afforded by the invention can also assist in providing a measure of blood flow velocity. During microwave renal artery denervation, injection of room temperature fluid into the renal artery from the guiding sheath creates transient reductions in catheter temperature. Monitoring temperature against time provides useful information on transit times (from the guiding sheath exit to the thermocouple location) and thus renal arterial flow, and together with measures of blood pressure can be used to estimate renal microvascular resistance.

Figure 6:
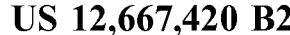

FIG. 6 provides an example of an in vivo microwave denervation procedure in a large animal model, and in particular illustrates changes in temperature during tuning of the microwave generating source in the range 2400-2500 MHz in order to find a frequency with maximum braid temperature rise (and thus minimal reflected power), and therefore optimize tissue coupling.

The referenced points and phases of the process are:
A' Initial baseline (blood temperature), approx. 37° C.
B' Catheter irrigation commenced (30 ml/m)
C' Microwave ablation commenced (110 W, 2400 MHz), from which point applied microwave frequency automatically increased to 2500 MHz over a period of 10 seconds; temperature increases rapidly
D' Peak temperature, achieved at 2450 MHz (associated with OW reflected power measured at generator)
E' Lowest measured temperature, indicating poor coupling (associated with 12 W reflected power measured at generator)
F' Tuning completed on reaching 2500 MHz, at which point ablation continues at selected frequency of 2450 MHz Impedance Measurement to Monitor Vascular Calibre During Ablation Microwave heating is radiant and can penetrate deeply into tissue, so catheter devices of the type described in WO2016/197206 can perform deep circumferential ablation with sparing of injury to tissue adjacent to the flowing blood pool.

During microwave renal denervation procedures it is important to be able to monitor renal arterial calibre. Reductions in renal arterial calibre increase the risk of thermal arterial injury, as the arterial wall is brought closer to the microwave antenna and is thus exposed to more rapid heating, while the vascular contraction can result in a reduced arterial blood flow and thus a reduced rate of cooling. On the other hand, renal arterial dilatation can provide evidence of successful renal nerve ablation and provide a physiological endpoint to ensure effective therapy delivery.

The inventors have determined that monitoring the impedance of the blood pool around the microwave ablation catheter device 10 can provide a measure of vascular calibre. While impedance monitoring is known in cardiovascular procedures, this is generally for measuring changes in tissue impedance as the tissue heats.

Figure 7:
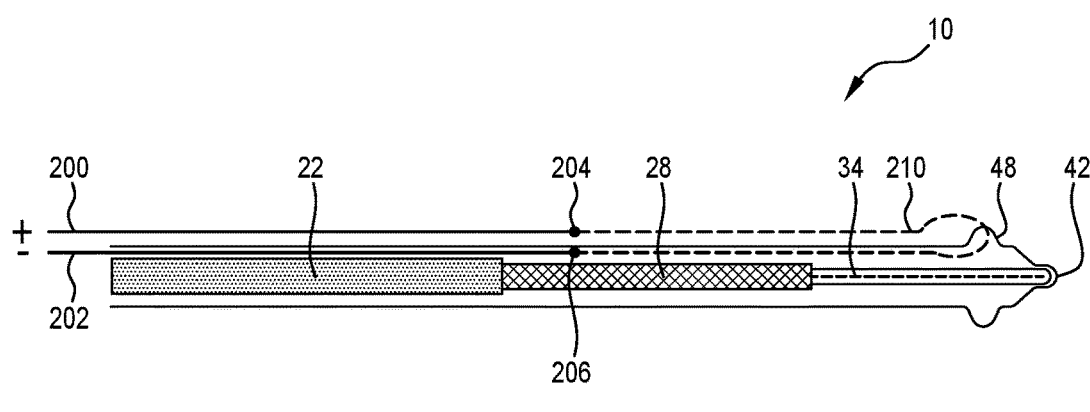
FIG. 7 shows diagrammatically a microwave ablation device including an impedance sensor arrangement.

As shown in FIG. 7, an embodiment of device 10 includes two electrodes 204, 206, respectively positioned on the outside and the inside of catheter outer sheath 46, at approximately the same axial position, proximal of the catheter radiator portion. In a first form, these electrodes are provided as the stripped ends of wires 200 and 202 that run the length of the catheter from the proximal end.

Wires 200 and 202 connect via suitable connectors in handle H to patient cable 52 and from there through electrical cabling 58 to electrical power/control unit 60, which includes appropriate circuitry and processing means to measure, record and provide display of the impedance between electrodes 204 and 206.

Once an alternating electrical potential is applied to wires 200 and 202, with the catheter within the blood pool and the saline irrigation fluid filling the catheter distal portion, an ionic conductivity path 210 is formed from electrode 206, along the inside of the catheter in the fluid volume surrounding feedline 22 and radiator 24, through one or more of the six slit orifices 50, and back along the outside of the catheter in the blood to electrode 204. Measuring the current flow thus provides a measure of the impedance between electrodes 204 and 206, namely the impedance of the saline volume and the blood volume through which the electrical path passes, and changes in this impedance can provide an indication of changes in the vessel calibre. As will be understood, as artery 12 expands during a denervation procedure, the electrical characteristics of the part of the electric circuit inside the catheter do not substantially change, but the lower resistive path of the part of the circuit outside the catheter has a noticeable effect on the overall impedance.

Figure 8:
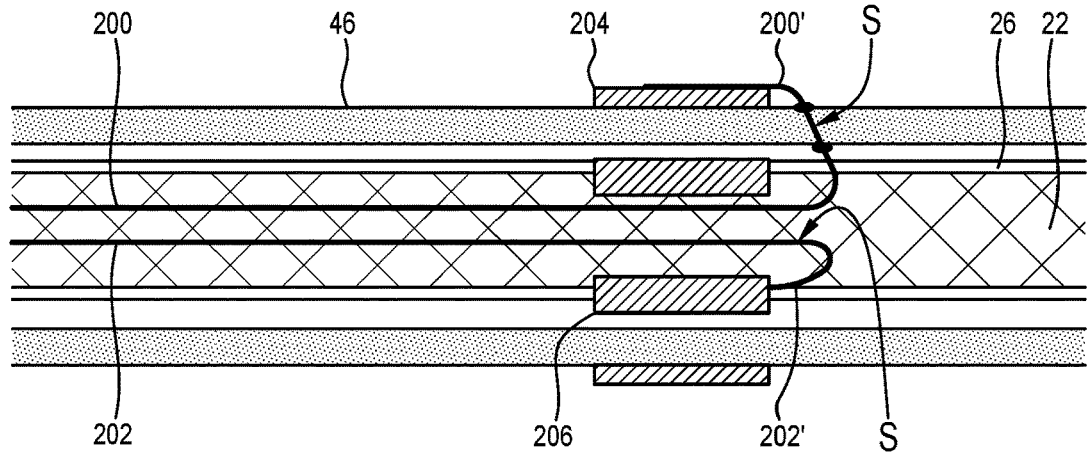
FIGS. 8 and 9 illustrate alternative embodiments of the sensing electrodes of FIG. 7.
Figure 9:
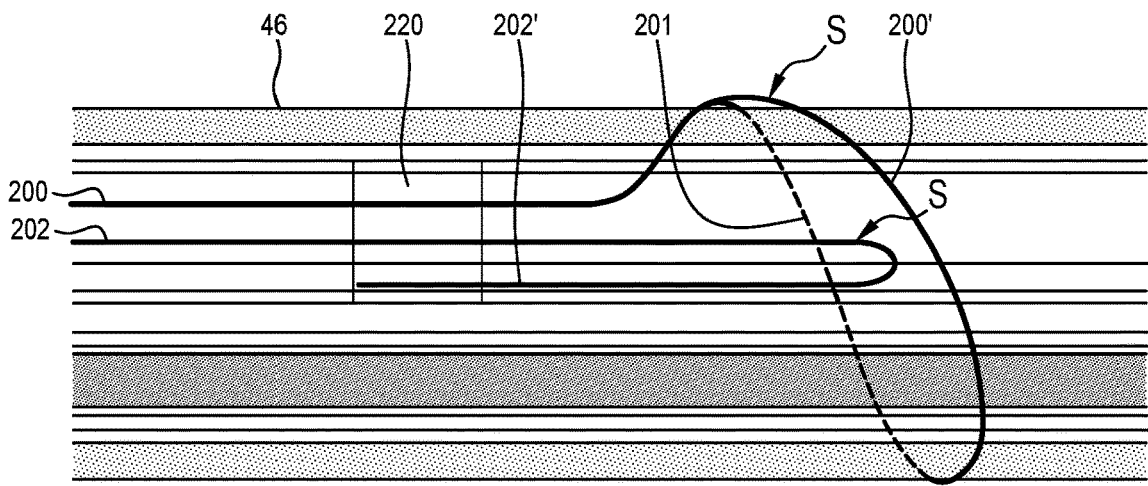

Hence, it is necessary that external electrode 204 is in the blood flow, and FIGS. 8 and 9 provide detail of suitable alternative ways of realizing the electrodes. In these figures, the reference S indicates the start of the terminal portion of wires 200 and 202 where the insulation is removed.

In FIG. 8, wire 202 runs along the catheter in the space between catheter sheath 46 and feedline sheath 26, its stripped end portion 202' bent back on itself by 180° and its tip then electrically connected and secured to ring electrode 206 around feedline sheath 26. Wire 200 similarly runs along the catheter in the space between catheter sheath 46 and feedline sheath 26, its stripped end portion 200' passing through a puncture in sheath 46, bent back on itself and its tip then electrically connected and secured to external ring electrode 204 around catheter sheath 46, such that both ring electrodes are longitudinally coincident at a position approximately 10-15 mm from the end of the feedline braid 28 (the proximal end of antenna 34). A suitable adhesive is used to seal the puncture hole.

In an alternative form, external electrode 204 may be provided in a manner independent of device 10. For example, it may be disposed at or near the distal end of guiding sheath 150 (for example, adjacent to the position where a radiopaque ring is commonly located), or it may be provided as a reference patient return electrode at a suitable location. Generally, such solutions are not the preferable approach, as they necessitate use of a separate electrical connection lead to the impedance measuring circuitry of electrical power/control unit 60. However, such an arrangement can have the advantage of reducing and simplifying the componentry of device 10, so minimizing the calibre of the catheter sheath 46.

As will be understood, it is important to terminate wires 200 and 202 before the radiator portion of the catheter, to ensure any metal components are positioned outside the microwave field and to avoid interference on both the field application and the impedance circuit that would otherwise result. Further, ring electrodes 204 and 206 are preferably not complete conducting rings, i.e. are preferably C-shaped rather than O-shaped, to avoid closing the electrical path, potentially rendering them parasitic inductors in the microwave field, which could lead to unwanted heating.

The alternative electrode arrangement in FIG. 9 includes internal electrode 206 as the terminal part 202' of wire 202, bent back on itself by 180° and its tip simply secured around feedline sheath 26 by heat shrink 220. Wire 200 passes through a puncture in sheath 46, and external electrode 204 comprises a loop 201 of the stripped wire end portion 200', passed around the outside of catheter sheath 46 and secured thereto by heat shrink or adhesive. The loop form of electrode 204—in both of the variants illustrated in FIGS. 8 and 9—ensures electrical contact with the blood pool, and the loop does not electrically connect back to itself (the return point shown in FIG. 9 is proximal of the start of the stripped insulation), to avoid closing the electrical path around the loop and the associated risk of inductive heating by the microwave field, as discussed above with reference to the embodiment of FIG. 8.

During their course along the outside of feedline sheath 26, wires 200, 202 may be secured thereto by glue joints or bands of heat shrink.

In a further embodiment of the present invention, the inventors developed and tested an alternative version of catheter 10 in which wires 200, 202 were integrated within the wall material of catheter sheath 46 at fabrication, thus wholly electrically insulated from the inside or outside of the sheath. In this version, electrodes 204 and 206 were formed as incomplete ring structures (of similar form to those of the embodiment shown in FIG. 8), one integrated (by melt-embedding) in the exterior surface of the catheter sheath wall, one in the interior surface. Like the wires, these electrodes were formed at fabrication of sheath 46, to present outer and inner surfaces, respectively, flush with the corresponding surfaces of the sheath wall, so to prevent any undesirable surface discontinuities.

One advantage of providing both electrodes on the catheter sheath 46 is to ensure the intervening distance is functionally constant, regardless of any relative movement of the feedline within, thus avoiding any associated measurement artefact.

Impedance Measurement—Trials and Results

Figures 10A, 10B, 11:
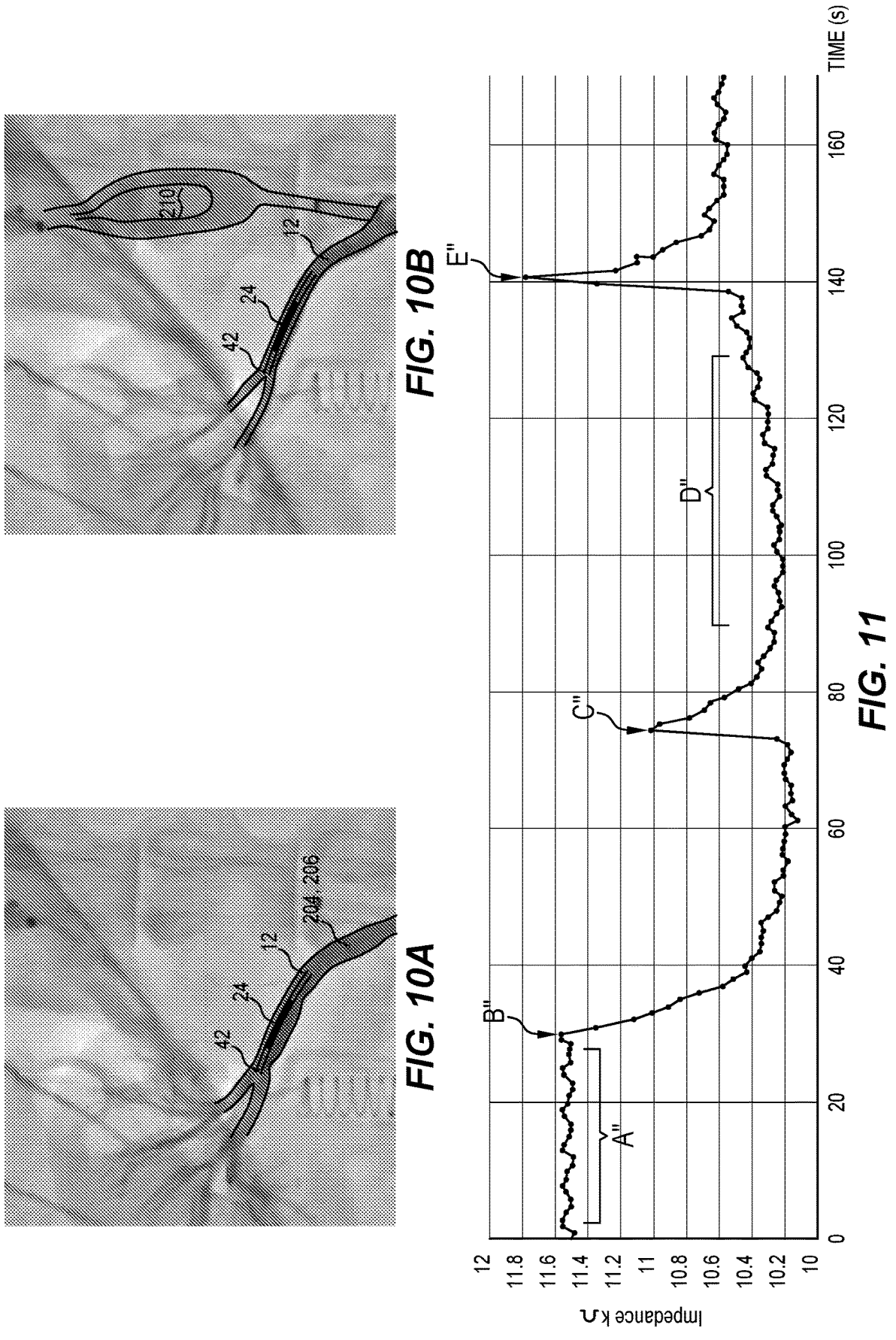
FIGS. 10A and 10B show angiograms at different stages of a trial of the device of FIG. 7, with FIG. 11 showing a time-impedance graph of the trial.

The concept of monitoring vascular dilatation using an impedance circuit in a denervation catheter was tested by the inventors in animal trials, the graphical output of impedance against time shown in FIG. 11.

The referenced points and phases of the procedure are:
A" Baseline (fluctuations of arterial size corresponding to respiration and changes in intra-abdominal pressure)
B" Ablation start
C" Angiogram 1 (FIG. 10A)
D" Balloon occlusion
E" Angiogram (FIG. 10B)

Impedance drop results from the heating effect of microwave radiation on the fluid, but impedance increases with increased rates of irrigation due to the cooling effect of room temperature saline. From the start of the microwave ablation at the end of phase A" the impedance drops for around 30 s, due to the warming of the saline around the microwave radiator.

At about 72 s the injection of cold contrast media causes the steep transient in measured impedance to point C", where the first angiogram is taken. FIG. 10 shows the position of radiator 24, catheter tip 42 and electrodes 204, 206 in the renal artery 12.

At this point, balloon occlusion of the suprarenal descending aorta (balloon occlusion device 210 shown in FIG. 10B) results in blood pressure drop and hence mild collapse of renal artery 12. This vascular contraction clearly translates as rising impedance during phase D" of the procedure.

The second angiogram corresponds to point E" in FIG. 11, which also shows contracted artery 12.

In this example, an impedance change of approximately 250 ohms was observed, with a reduction of vessel calibre from approximately 6 mm to 5 mm.

This experiment clearly demonstrates the value of impedance monitoring as a measure of vascular calibre, and hence its value as a feedback mechanism in vascular denervation therapy.

In addition to providing an indication of the points and phases in the procedure discussed above, the invention can provide an indication of deployment of the locating formation(s) 48, provided the fluid path traverses the position of a formation. Once a locating formation is deployed, then any observed change in impedance should be due solely to vascular calibre change. But during deployment the impedance is sensitive to the distension of the locating formation, and the invention can thus be used to confirm successful deployment.

It will be understood that the invention disclosed and defined in this specification extends to all alternative combinations of two or more of the individual features mentioned or evident from the text or drawings. All of these different combinations constitute various alternative aspects of the invention.

As used herein, except where the context requires otherwise, the term "comprise" and variations of the term, such as "comprising", "comprises" and "comprised", are not intended to exclude further additives, components, integers or steps.

What is claimed is:

1. A microwave catheter ablation device for delivery of energy to a selected region of tissue, the microwave catheter ablation device comprising:
   an electrical feedline;
   an antenna portion including a radiating antenna electrically connectable via the electrical feedline to a microwave generator and configured to generate an electromagnetic field comprising electromagnetic waves in a microwave energy spectrum able to ablate tissue in the selected region of tissue;
   an elongated catheter having a distal tip, an outer sheath and one or more orifices formed through the outer sheath in or adjacent to the antenna portion, wherein the outer sheath is configured to allow a flow of fluid along the catheter to exit through the one or more orifices; and an impedance monitoring system comprising first and second electrodes positioned along a length of the catheter at locations spaced apart from the distal tip, wherein the first and second electrodes are arranged respectively inside and outside the outer sheath and configured such that in use the impedance monitoring system applies an electrical signal to create an electric circuit incorporating an ionic conductivity path through the fluid between the first electrode and the second electrode via the one or more orifices and the impedance monitoring system measures the impedance of the ionic conductivity path;
   wherein the second electrode is separate to the radiating antenna.

2. The device of claim 1, wherein the first and second electrodes are arranged proximal of the antenna portion.

3. The device of claim 1, wherein the first and second electrodes are electrically connectable to an impedance monitor configured to provide an indication to a user of the device of a measure of an impedance of the electric circuit.

4. The device of claim 1, wherein one or both of the first and second electrodes comprise ring or part-ring form electrodes.

5. The device of claim 1, wherein the first electrode arranged on the inside of the outer sheath is supported on an outside surface of the electrical feedline.

6. The device of claim 1, wherein the second electrode arranged on the outside of the catheter sheath is supported on an outside surface of the catheter sheath.

7. The device of claim 1, wherein one or both of the first and second electrodes is embedded into a wall of the catheter sheath.

8. The device of claim 1, wherein the outer catheter sheath is sized to provide sufficient internal free space around the feedline to allow a flow of fluid through the catheter from a proximal end and exiting the catheter through the one or more orifices at a distal end.

9. The device of claim 8 wherein the one or more orifices are arranged radially around the outer sheath.

10. The device of claim 1, wherein the first and second electrodes are positioned at approximately at the same axial position along the catheter.

11. The device of claim 1, wherein the ionic conductivity path extends within the catheter from the first electrode to the one or more orifices and extends from the one or more orifices to the second electrode outside of the catheter.

12. The device of claim 1, wherein the first and second electrodes are each formed by stripped ends of wires, the wires running a length of the catheter from a proximal end of the catheter.

* * * * *